United States Patent
Cuccia et al.

(10) Patent No.: US 9,883,803 B2
(45) Date of Patent: Feb. 6, 2018

(54) EFFICIENT MODULATED IMAGING

(71) Applicant: MODULATED IMAGING, INC., Irvine, CA (US)

(72) Inventors: David Cuccia, Costa Mesa, CA (US); Amaan Mazhar, Irvine, CA (US)

(73) Assignee: MODULATED IMAGING, INC., Irvine, CA (US)

( * ) Notice: Subject to any disclaimer, the term of this patent is extended or adjusted under 35 U.S.C. 154(b) by 454 days.

(21) Appl. No.: 14/538,776

(22) Filed: Nov. 11, 2014

(65) Prior Publication Data
US 2015/0141839 A1 May 21, 2015

Related U.S. Application Data

(63) Continuation of application No. 14/074,368, filed on Nov. 7, 2013, now Pat. No. 8,892,192.
(Continued)

(51) Int. Cl.
*A61B 6/00* (2006.01)
*A61B 5/00* (2006.01)

(52) U.S. Cl.
CPC .......... *A61B 5/0064* (2013.01); *A61B 5/0071* (2013.01); *A61B 5/0077* (2013.01)

(58) Field of Classification Search
CPC ...................................... A61B 5/0059–5/0077
(Continued)

(56) References Cited

U.S. PATENT DOCUMENTS 4,286,602 A 9/1981 Guy
4,407,290 A 10/1983 Wilber
(Continued)

FOREIGN PATENT DOCUMENTS

EP 13852589.4 5/2016
WO WO 89/12223 A1 12/1989
(Continued)

OTHER PUBLICATIONS

"Wound imaging, measurement and healing progress documentation", retrieved from http://www.aranzmedical.com/wound-assessment/.
Bélanger, Samuel, et al., "Real-time diffuse optical tomography based on structured illumination", Journal of Biomedical Optics, 15(1), 016006-1-016006-7 (2010).
Bevilacqua, Frédéric, et al., "Broadband absorption spectroscopy in turbid media by combined frequency-domain and steady-state methods," Applied Optics, 39(34), pp. 6498-6507 (2000).
(Continued)

*Primary Examiner* — Amanda Patton
*Assistant Examiner* — Philip C Edwards
(74) *Attorney, Agent, or Firm* — ONE LLP

(57) ABSTRACT

An apparatus for turbid sample measurement comprising a plurality of light sources for illuminating a turbid sample target area with non-spatial structured light, a projection system for illuminating the turbid sample target area with spatial structured light, a sensor for collecting light from the turbid sample target area, and a processor to analyze the data captured by the sensor to yield scattering and absorption coefficients of the turbid sample. A method comprises illuminating the sample with spatial structured light, collecting light reflected from the sample at a number of wavelengths, illuminating the sample with non-spatial structured light, collecting light reflected from the sample at a number of wavelengths, and combining the measurements of the collected light to obtain the optical properties of the sample and/or the concentration of absorbing or fluorescent molecules. The wavelengths of the spatial and non-spatial light sources are preferably different.

7 Claims, 12 Drawing Sheets

Related U.S. Application Data

(60) Provisional application No. 61/793,331, filed on Mar. 15, 2013, provisional application No. 61/723,721, filed on Nov. 7, 2012.

(58) Field of Classification Search
USPC .................................................. 600/476
See application file for complete search history.

(56) References Cited

U.S. PATENT DOCUMENTS

| | | |
|---|---|---|
| 4,515,165 A | 5/1985 | Carroll |
| 4,600,011 A | 7/1986 | Watmough |
| 5,057,695 A | 10/1991 | Hirao et al. |
| 5,140,463 A | 8/1992 | Yoo et al. |
| 5,142,372 A | 8/1992 | Alfano et al. |
| 5,203,339 A | 4/1993 | Knüttel et al. |
| 5,227,912 A | 7/1993 | Ho et al. |
| 5,275,168 A | 1/1994 | Reintjes et al. |
| 5,277,181 A | 1/1994 | Mendelson et al. |
| 5,299,035 A | 3/1994 | Leith et al. |
| 5,349,951 A | 9/1994 | Ito et al. |
| 5,353,799 A | 10/1994 | Chance |
| 5,369,496 A | 11/1994 | Alfano et al. |
| 5,371,368 A | 12/1994 | Alfano et al. |
| 5,416,582 A | 5/1995 | Knutson et al. |
| 5,418,797 A | 5/1995 | Bashkansky et al. |
| 5,625,458 A | 4/1997 | Alfano et al. |
| 5,640,247 A | 6/1997 | Tsuchiya et al. |
| 5,722,406 A | 3/1998 | Papaioannou |
| 5,762,607 A | 6/1998 | Schotland et al. |
| 5,865,754 A | 2/1999 | Sevick-Muraca et al. |
| 5,903,357 A | 5/1999 | Colak |
| 5,928,137 A | 7/1999 | Green |
| 5,931,789 A | 8/1999 | Alfano et al. |
| 5,969,822 A | 10/1999 | Fright et al. |
| 5,987,351 A | 11/1999 | Chance |
| 6,032,070 A | 2/2000 | Flock et al. |
| 6,076,010 A | 6/2000 | Boas et al. |
| 6,081,322 A | 6/2000 | Barbour |
| 6,091,984 A | 7/2000 | Perelman et al. |
| 6,104,946 A | 8/2000 | Tsuchiya et al. |
| 6,108,576 A | 8/2000 | Alfano et al. |
| 6,122,042 A | 9/2000 | Wunderman et al. |
| 6,148,226 A | 11/2000 | Painchaud et al. |
| 6,208,415 B1 | 3/2001 | De Boer et al. |
| 6,208,886 B1 | 3/2001 | Alfano et al. |
| 6,240,312 B1 | 5/2001 | Alfano et al. |
| 6,321,111 B1 | 11/2001 | Perelman et al. |
| 6,327,489 B1 | 12/2001 | Hoogenraad et al. |
| 6,332,093 B1 | 12/2001 | Painchaud et al. |
| 6,335,792 B1 | 1/2002 | Tsuchiya |
| 6,348,942 B1 | 2/2002 | Watkins |
| 6,404,497 B1 | 6/2002 | Backman et al. |
| 6,405,069 B1 | 6/2002 | Oraevsky et al. |
| 6,549,284 B1 | 4/2003 | Boas et al. |
| 6,618,614 B1 | 9/2003 | Chance |
| 6,624,890 B2 | 9/2003 | Backman et al. |
| 6,678,541 B1 | 1/2004 | Durkin et al. |
| 6,754,518 B1 | 6/2004 | Lloyd et al. |
| 6,795,195 B1 | 9/2004 | Barbour et al. |
| 6,825,928 B2 | 11/2004 | Liu et al. |
| 6,922,583 B1 | 7/2005 | Perelman et al. |
| RE38,800 E | 9/2005 | Barbour |
| 6,958,815 B2 | 10/2005 | Bevilacqua et al. |
| 7,046,832 B1 | 5/2006 | Barbour |
| 7,139,603 B2 | 11/2006 | Chance |
| 7,224,905 B2 | 5/2007 | Ruggiero |
| 7,274,446 B2 | 9/2007 | Wolleschensky et al. |
| 7,304,724 B2 | 12/2007 | Durkin et al. |
| 7,418,118 B2 | 8/2008 | Furnas et al. |
| 7,428,434 B2 | 9/2008 | Tromberg et al. |
| 7,610,082 B2 | 10/2009 | Chance |
| 7,627,365 B2 | 12/2009 | Chance |
| 7,637,893 B2 | 12/2009 | Christensen et al. |
| 7,647,091 B2 | 1/2010 | Ntziachristos et al. |
| 7,652,763 B2 | 1/2010 | Matousek et al. |
| 7,692,160 B2 | 4/2010 | Lee et al. |
| 7,717,888 B2 | 5/2010 | Vaillancourt et al. |
| 7,729,750 B2 | 6/2010 | Tromberg et al. |
| RE41,949 E | 11/2010 | Barbour et al. |
| 7,873,407 B2 | 1/2011 | Levenson et al. |
| 7,904,139 B2 | 3/2011 | Chance |
| 7,911,604 B2 | 3/2011 | Matousek et al. |
| 7,962,200 B2 | 6/2011 | Ntziachristos et al. |
| 7,983,741 B2 | 7/2011 | Chance |
| 8,014,569 B2 | 9/2011 | Durkin et al. |
| 8,082,015 B2 | 12/2011 | Yodh et al. |
| 8,085,396 B2 | 12/2011 | Matousek et al. |
| 8,103,331 B2 | 1/2012 | Hoyt et al. |
| 8,159,664 B2 | 4/2012 | Matousek et al. |
| 8,243,269 B2 | 4/2012 | Matousek et al. |
| 8,170,651 B2 | 5/2012 | Ripoll Lorenzo et al. |
| 8,185,176 B2 | 5/2012 | Mangat et al. |
| D662,122 S | 6/2012 | Goodwin et al. |
| 8,199,322 B2 | 6/2012 | Kashyap et al. |
| 8,259,902 B2 | 9/2012 | Matousek et al. |
| 8,276,287 B2 | 10/2012 | Estocado |
| 8,301,216 B2 | 10/2012 | Durkin et al. |
| 8,310,532 B2 | 11/2012 | Mertz et al. |
| 8,326,406 B2 | 12/2012 | Ntziachristos et al. |
| 8,360,321 B2 | 1/2013 | Lee et al. |
| 8,505,209 B2 | 8/2013 | Estocado |
| 8,509,879 B2 | 8/2013 | Durkin et al. |
| 8,606,032 B2 | 12/2013 | Nishi et al. |
| 2003/0002028 A1 | 1/2003 | Rice et al. |
| 2003/0023172 A1 | 1/2003 | Tromberg et al. |
| 2003/0184757 A1 | 10/2003 | Bevilacqua et al. |
| 2004/0095576 A1 | 5/2004 | Wolleschensky |
| 2006/0029350 A1 | 2/2006 | Chung et al. |
| 2006/0155195 A1 | 7/2006 | Maier et al. |
| 2006/0247532 A1 | 11/2006 | Ramanujam et al. |
| 2006/0268241 A1 | 11/2006 | Watson et al. |
| 2008/0101657 A1 | 5/2008 | Durkin et al. |
| 2009/0118622 A1* | 5/2009 | Durkin ............... A61B 5/0073 600/473 |
| 2010/0210931 A1 | 2/2010 | Van Der Brug et al. |
| 2010/0101069 A1 | 4/2010 | Christensen et al. |
| 2010/0160754 A1 | 6/2010 | Durkin et al. |
| 2010/0191321 A1 | 7/2010 | Schlun et al. |
| 2010/0049056 A1 | 8/2010 | Cuccia et al. |
| 2011/0124988 A1 | 5/2011 | Cuccia |
| 2011/0149163 A1 | 6/2011 | Nishi et al. |
| 2011/0284639 A1 | 11/2011 | Lee et al. |
| 2012/0236310 A1 | 9/2012 | Lesage et al. |
| 2012/0277559 A1 | 11/2012 | Kohl-Bareis et al. |
| 2013/0237841 A1 | 9/2013 | Freeman et al. |
| 2013/0274612 A1 | 10/2013 | Cuccia |
| 2013/0331708 A1 | 12/2013 | Estocado |
| 2013/0345560 A1 | 12/2013 | Ferguson, Jr. et al. |

FOREIGN PATENT DOCUMENTS

| | | |
|---|---|---|
| WO | WO 93/00045 A1 | 1/1993 |
| WO | WO 99/20997 A1 | 4/1999 |
| WO | WO 00/20843 A1 | 4/2000 |
| WO | WO 01/19241 A1 | 3/2001 |
| WO | WO 01/020546 A2 | 3/2001 |
| WO | WO 2004/069042 A2 | 8/2004 |
| WO | WO 2005/008195 A2 | 1/2005 |
| WO | WO 2006/061566 A1 | 6/2006 |
| WO | WO 2008/151159 A2 | 12/2008 |
| WO | WO 2011/035408 A1 | 3/2011 |
| WO | PCT/US13/68956 | 2/2014 |
| WO | PCT/US2013/068956 | 5/2015 |

OTHER PUBLICATIONS

Blot, S. I., et al., "The Use of Laser Doppler Imaging in Measuring Wound-Healing Progress," Arch. Surg., vol. 136, p. 116 (2001).

Chen, M. H., et al., "Development of a Thermal and Hyperspectral Imaging System for Wound Characterization and Metabolic Correlation", Johns Hopkins APL Technical Digest, vol. 26, No. 1, pp. 67-74 (2005).

(56) References Cited

OTHER PUBLICATIONS

Cuccia, D. J., et al., "Quantitation and mapping of tissue optical properties using modulated imaging", Journal of Biomedical Optics, 14(2), pp. 024012-1-024012-13 (2009).
Gebhart, S. C., et al., "Liquid-crystal tunable filter spectral imaging for brain tumor demarcation", Applied Optics, 46(10), pp. 1896-1910 (2007).
"Hyperspectral Imaging: Shedding New Light on Wound Healing", retrieved from http://www.nist.gov/pml/div685/hyperspectral.cfm.
Hale, G. M., et al., "Optical Constants of Water in the 200-nm to 200-µm Wavelength Region", Applied Optics, 12(3), pp. 555-563 (1973).
Harper, J. R., "Wound Care: What's the Latest?", ACP/IMDA Scientific Meeting, pp. 1-59 (2011).
Haskell, R. C., et al., "Boundary conditions for the diffusion equation in radiative transfer", J. Opt. Soc. Am., 11(10), pp. 2727-2741 (1994).
"Wound Image Analysis Guide for Clinicians", retrieved from www.InfoVACTherapy.com (2008).
Jacques, Steven L., "Melanosome absorption coefficient", retrieved from http://omlc.ogi.edu/spectra/melanin/mua.html, pp. 1-2 (1998).
Kobayashi, M., et al., "Analysis of nonlinear relation for skin hemoglobin imaging", Optics Express, 9(13), pp. 802-812 (2001).
Nishidate, Izumi, et al., "Estimation of melanin and hemoglobin in skin tissue using multiple regression analysis aided by Monte Carlo simulation", Journal of Biomedical Optics, 9(4), pp. 700-710 (2004).
Nourri, D., "Colour and multispectral imaging for wound healing evaluation in the context of a comparative preclinical study", published in Medical Imaging 2013: Image Processing, ake Buena Vista (Orlando Area), Florida: United States, pp. 1-10 (2013).
"SPY Imaging in the Treatment of Non-healing Wounds", retrieved from http://www.novadaq.com/procedures/wound-care.
"LUNA Flourescence Angiography for Wound Care", retrieved from http://www.novadaq.com/products/luna-flourescence-angiography.
Palmer, G. M., et al., "Monte Carlo-based inverse model for calculating tissue optical properties. Part I: Theory and validation on synthetic phantoms", Applied Optics, 45(5), pp. 1062-1071 (2006).
Prahl, Scott, "Optical Absorption of Hemoglobin", retrieved from http://omlc.ogi.edu/spectra/hemoglobin/index.html, pp. 1-3 (1999).
Rajaram, N., et al., "Lookup table-based inverse model for determining optical properties of turbid media", Journal of Biomedical Optics, 13(5), pp. 050501-1-050501-3 (2008).
Salcido, R., "Beyond Photography: Wound Imaging", Skin and Wound Care, vol. 24, No. 2, p. 56 (2011).
Simpson, C. R., et al. "Near-infrared optical properties of ex vivo human skin and subcutaneous tissues measured using the Monte Carlo inversion technique", Phys. Med. Biol., 43, pp. 2465-2478 (1998).
Dargaville, T. R., et al. "Sensors and Imaging for Wound Healing: A Review", Biosensors and Bioelectronics, vol. 41, pp. 30-42 (2013).
"Scout", retrieved from http://www.woundvision/scout/.
Tseng, Sheng-Hao, et al., "In vivo determination of skin near-infrared optical properties using diffuse optical spectroscopy", Journal of Biomedical Optics, 13(1), pp. 014016-1-041016-7 (2008).
Van Staveren, H. J., et al., "Light scattering in Intralipid-10% in the wavelength range of 400-1100 nm", Applied Optics, 30(31), pp. 4507-4514 (1991).
Weber, J. R., et al., "Noncontact imaging of absorption and scattering in layered tissue using spatially modulated structured light", Journal of Applied Physics, 105, pp. 102028-1-102028-9 (2009).
Yudovsky, D., et al. "Hyperspectral Imaging in Diabetic Foot Wound Care", Journal of Diabetes Science and Technology, vol. 4, No. 5, pp. 1099-1113 (2010).
Zhou, A. H., "A Survey of Optical Imaging Techniques for Assessing Wound Healing", Intl. Journal of Intelligent Control and Systems, vol. 17, No. 3, pp. 79-85 (2012).

\* cited by examiner

EFFICIENT MODULATED IMAGING

REFERENCE TO RELATED APPLICATIONS

This application is a continuation of U.S. patent application Ser. No. 14/074,368, filed Nov. 7, 2013, which claims the benefit of U.S. Provisional Application No. 61/793,331, filed Mar. 15, 2013, and U.S. Provisional Application No. 61/723,721, filed Nov. 7, 2012, which applications are incorporated by reference.

FIELD

The embodiments described herein generally relate to modulated imaging for quantitative characterization of tissue structure and function and, more particularly, to systems and methods that facilitate efficient modulated imaging.

BACKGROUND

Quantitative characterization of tissue structure and function is one of the most challenging problems in medical imaging. Diffuse optical methods can be used to measure biological tissues or other turbid (i.e. light-scattering) samples with resolution and depth sensitivity from microns to centimeter length scales, limited by fundamental light-tissue interactions. Important tissue components (referred to as chromophores) such as oxy-hemoglobin, deoxy-hemoglobin and water can be detected optically and correlate to various indicators or indices of local tissue health or physiological status. Examples of such indices include the tissue oxygen saturation ($stO_2$, or fraction of oxygenated blood), total blood volume (ctTHb), tissue water fraction ($ctH_2O$), and tissue perfusion or metabolism. These indices can provide a powerful means for physicians to perform diagnoses and/or guide therapies. These chromophores can be detected because they have absorption spectra with detectable features, in the visible and/or near infrared regions. In essence, a light source can be used to illuminate a tissue sample, and the remitted light can be used to measure the absorption features in tissue and quantify the chromophore of interest. Practically, this is a difficult measurement due to the presence of scattering in tissue. A class of probe-based technologies have been described in academia and have also been translated commercially by a number of companies (Somanetics, Hutchinson, ViOptix). Each of these technologies use a number of different algorithms and hardware components (illumination sources, spectral detection) to approach the problem to account, correct, or control for tissue scattering to derive meaningful information about hemoglobin and tissue oxygenation. These probes take advantage of the large selection of single point detectors that enable spectral flexibility and high sensitivity. However, contact probes suffer from some major limitations. By nature, contact probes are not imaging technologies and thus not ideal for assessing large areas of tissue. This is important because tissue health is often spatially variant, for example, in tissue wounds (burns, ulcers, skin flaps, etc.), where spatial contrast can be present both between normal tissue and the wound, as well as within the wound itself (e.g. wound boundary vs. wound center). With contact probes, in order to synthesize a low resolution image, multiple contact probes must be placed in a number of tissue locations, or the probe must be scanned across the surface. Typical wounds can vary from a few mm in size to many cm, presenting a challenge for probe technologies to design for, address, and/or adapt to this large range.

Camera based optical spectral imaging methods have also been developed in academia and commercially. A multispectral imaging technology using visible light (HyperMed) has been applied to measure tissue oxygenation over a wide field of view (~10 cm×10 cm) and has been applied to monitoring of diabetic wounds. Multi-spectral imaging methods typically employ wavelengths which sample only top superficial (<1 mm deep) layers of tissue. While near-infrared (650-1000 nm) penetrates much more deeply, the chromophore contrast in the reflected or transmitted light signal is more challenging to isolate and quantify, due to the presence of a strong tissue scattering coefficient (i.e. compared to absorption). A technology that can overcome this limitation and assesses tissue health over a wide field of view in a non-contact manner both in superficial layers (~100 um deep) as well as subsurface layers (1-10 mm) is more valuable and is therefore desired.

A novel optical imaging method called Modulated Imaging (MI), which enables quantitative analysis of disease progression and therapeutic response in a wide field of view and depth of the tissue without requiring direct contact, was recently introduced. MI has been described in U.S. Pat. No. 6,958,815 B2, herein referred to as Bevilacqua et al, which is incorporated herein by reference. This technique comprises illuminating biological tissue or other turbid medium (a sample that is both scattering and absorbing) with a spatially modulated light (or "structured light") pattern at one or more optical wavelengths and analyzing the resulting collected back reflected and scattered light from the tissue. A preferred embodiment of MI is called Spatial Frequency Domain Imaging (SFDI), in which the spatial light pattern, or structure, is sinusoidal, which provides an algorithmically simple way of detecting the structured light contrast from a small number (typically 3-15 per wavelength) of structured light measurements. When combined with multi-spectral imaging, the optical properties at two or more wavelengths can be used to quantitatively determine the in-vivo concentrations of chromophores that are relevant to tissue health, e.g. oxy-hemoglobin ($ctO_2Hb$), deoxy-hemoglobin (ctHHb) and water ($ctH_2O$).

In order to perform spectroscopic (wavelength-dependent) measurements of absorbing chromophores, the MI technique requires collection of remitted spatially structured light from tissue at various wavelengths. This has been accomplished to-date by repeating the disclosed technique of Bevilacqua et al for each desired wavelength. Thus, total imaging times scale directly with the number of wavelengths measured. This can be particularly challenging for some wavelengths in the near-infrared where illumination sources are less bright, optical throughput is low, and detector quantum efficiencies are low due to CCD limitations. For low throughput wavelengths, long integration times (10s to 100s of ms) are required to obtain adequate signal to noise ratio. Light intensity must be increased at those wavelengths in order to reduce integration time. However, this is limited by the etendue, or light throughput, limitations of structured light projection hardware, including that of both light source (e.g. LEDs, lasers, white light bulb), optical relay system (e.g. lenses, waveguides, mirrors), and pattern generation technology (e.g. reflective digital micromirror array or liquid-crystal-on-silicon, patterned transmissive material or LCD array, or holographic element). "Brute force" increases in intensity of weak or inefficient wavelength bands can have other effects including increased power consumption, increased thermal stress (which can lead to further source inefficiency and instability) and increased cooling requirements. Longer imaging times also create a practical issue in medical (or other motion-sensitive) applications as it leads to artifacts in the final image due to small movements of the measurement sample (e.g. tissue) under study. It is therefore desirable to provide an apparatus and method that improves the capability of the current modulated imaging methods while maintaining accuracy but improving system efficiency and reducing the imaging time.

As described briefly above, MI comprises illumination of a sample with one or more spatially structured intensity patterns over a large (many $cm^2$) area of a tissue (or other turbid) sample and collecting and analyzing the resulting light received back from the sample. An analysis of the amplitude and/or phase of the spatially-structured light received back from the sample as a function of spatial frequency or periodicity, often referred to as the modulation transfer function (MTF) can be used to determine the sample's optical property information at any discrete wavelength. Examples of tissue optical properties include light absorption, light scattering (magnitude and/or angular-dependence), and light fluorescence. Analysis of this light-dependent data (model based or empirically-derived) can be used to generate 2D or 3D maps of the quantitative absorption ($\mu_a$) and reduced scattering ($\mu_s'$) optical properties. Region-wise (multi-pixel) assessments can also be produced by averaging or otherwise accumulating multiple spatial optical property or derived results. By using the spatial frequency or periodicity information at various wavelengths, MI can separate absorption ($\mu_a$) and fluorescence ($\mu_a$) from scattering ($\mu_s$) effects, which each result from physically distinct contrast mechanisms.

Mapping the absorption coefficient, ($\mu_a$), at multiple wavelengths, by MI, in turn, enables quantitative spectroscopy of tissue chromophores including but not limited to oxy- and deoxy-hemoglobin and water ($ctO_2Hb$, $ctHHb$, and $ctH_2O$) and derived physiology parameters such as tissue oxygen saturation and blood volume ($stO_2$ and $ctTHb$). The spatially-varying phase of the light collected from the tissue can also be simultaneously measured, and yields topological surface information. This combination of measurements enables visualization of the 3D tissue profile, as well as calibration data for accommodating curved surfaces in the analysis. A typical data flow is shown in FIG. 1.

A present issue in measurement and analysis of MI is imaging time. Longer imaging times increase sensitivity to motion and ambient lighting, which can result in artifacts in the two dimensional maps of the measured biological metrics—particularly in clinical applications. Hardware limitations are a key cause for long imaging times. High power light sources, such as light emitting diodes (LEDs), can ameliorate the issue but measurement time remains an issue in the near infrared. This is because LED power and camera sensitivity can depend strongly on wavelength and LED power is limited by cooling requirements and size of the apparatus.

FIG. 2 shows an example dataset of an infant burn wound, collected with a prior art modulated imaging apparatus which exhibits motion artifacts. FIG. 2(b) shows reflectance data versus wavelength and spatial frequency. Note the artifact high spatial frequency striped pattern in the demodulated 970 nm data (right, bottom). Here the term demodulated data means the extracted amplitude of the light received from the tissue normalized to the amplitude of the light illumination at each spatial frequency. In other words the demodulated data is the modulation transfer function of the illuminated tissue. These artifacts are due to motion during the long integration times required for this wavelength. As FIG. 2(c) highlights, a 10× longer integration time (i.e. 5 s) is required to acquire the data set at 970 nm compared to other shorter wavelengths (i.e. only 0.5 s). Using all wavelength information to produce chromophore or scattering amplitude/slope measurements results in sinusoidal artifacts in the derived data as shown in average scatter amplitude image in FIG. 2(d).

It has been shown that if the 970 nm wavelength measurement (and thus analysis of water concentration ($ctH2O$)) is excluded $ctO_2Hb$ and $ctHHb$ can still be accurately calculated by assuming a typical tissue water fraction. FIG. 2(e) shows the resulting analysis when 970 nm data are excluded which correctly identifies a high-scattering region in the upper left corner of the infant's arm, indicated by the black arrow. This region corresponds to the most severe location of the burn and is useful to identify. However, water sensitivity is highly desirable in many studies, so excluding 970 nm data is not desirable.

In general, therefore, it is desirable to have the flexibility to capture spectral contrast measurements of target chromophores at various wavelengths, while simultaneously having minimal increases in complexity, if any, to the structured light requirements of the core modulated imaging technique. It is therefore desirable to provide an apparatus and a method to remove the effects of artifacts at wavelengths with poor performance/sensitivity in order to provide full information about the concentrations and/or distributions of all relevant components including $ctH_2O$, $ctO_2Hb$, $ctHHb$, and others (e.g. bilirubin, methemoglobin, lipids, exogenous agents).

SUMMARY

The embodiments provided herein are directed to systems and methods that facilitate efficient modulated imaging for quantitative characterization of tissue structure and function. In one embodiment, an apparatus for the measurement of a turbid sample comprises an illumination apparatus having a plurality of light sources configured to illuminate a target area of a turbid sample with light not having spatial structure, a projection system configured to illuminate the target area of turbid sample with light having spatial structure, a sensor configured to collect light from the target area of the turbid sample, and a processor configured to analyze the data captured by the sensor to yield the scattering and absorption coefficients of the turbid sample. The light sources configured to illuminate the sample with light not having spatial structure are arranged on the perimeter of the illumination apparatus. The projection system comprises a number of switchable light sources. The wavelengths of the light sources without spatial structure are preferably different from the wavelengths of the light having spatial structure.

In another embodiment, a method for the measurement of a turbid sample comprises illuminating the sample with light having spatial structure, collecting light reflected from the sample to obtain the remitted light of the sample at a number of wavelengths, $\lambda_j$, illuminating the sample with light not having spatial structure, collecting light reflected from the sample to obtain the remitted light of the sample at a number of wavelengths, $\lambda_k$, and combining the obtained measurements from light having spatial structure and light not having spatial structure to obtain fit parameters, including the optical properties of the sample at wavelengths $\lambda_j$, and/or the concentration of absorbing or fluorescent molecules.

The wavelengths, $\lambda_k$, of the light not having spatial structure is preferably different from the wavelengths of light having spatial structure, $\lambda_j$, i.e., $\lambda_k \neq \lambda_j$.

The combining of the obtained measurements is performed using a scattering function describing the dependence of scattering on wavelength to interpolate or extrapolate the measurements at discrete wavelengths, $\lambda_j$ obtained using light having spatial structure, in order to obtain estimates for scattering at wavelengths $\lambda_k$ obtained using light not having spatial structure.

The scattering function of wavelength is a power law function described as $\mu_s'(\lambda) = A_1 * \lambda^{-b}_1 + A_2 * \lambda^{-b}_2 + \ldots + A_n * \lambda^{-b}_n$.

The systems, methods, features and advantages of the invention will be or will become apparent to one with skill in the art upon examination of the following figures and detailed description. It is intended that all such additional methods, features and advantages be included within this description, be within the scope of the invention, and be protected by the accompanying claims. It is also intended that the invention is not limited to require the details of the example embodiments.

BRIEF DESCRIPTION OF THE FIGURES

The accompanying drawings, which are included as part of the present specification, illustrate the presently preferred embodiment and, together with the general description given above and the detailed description of the preferred embodiment given below, serve to explain and teach the principles of the present invention.

Figure 1:
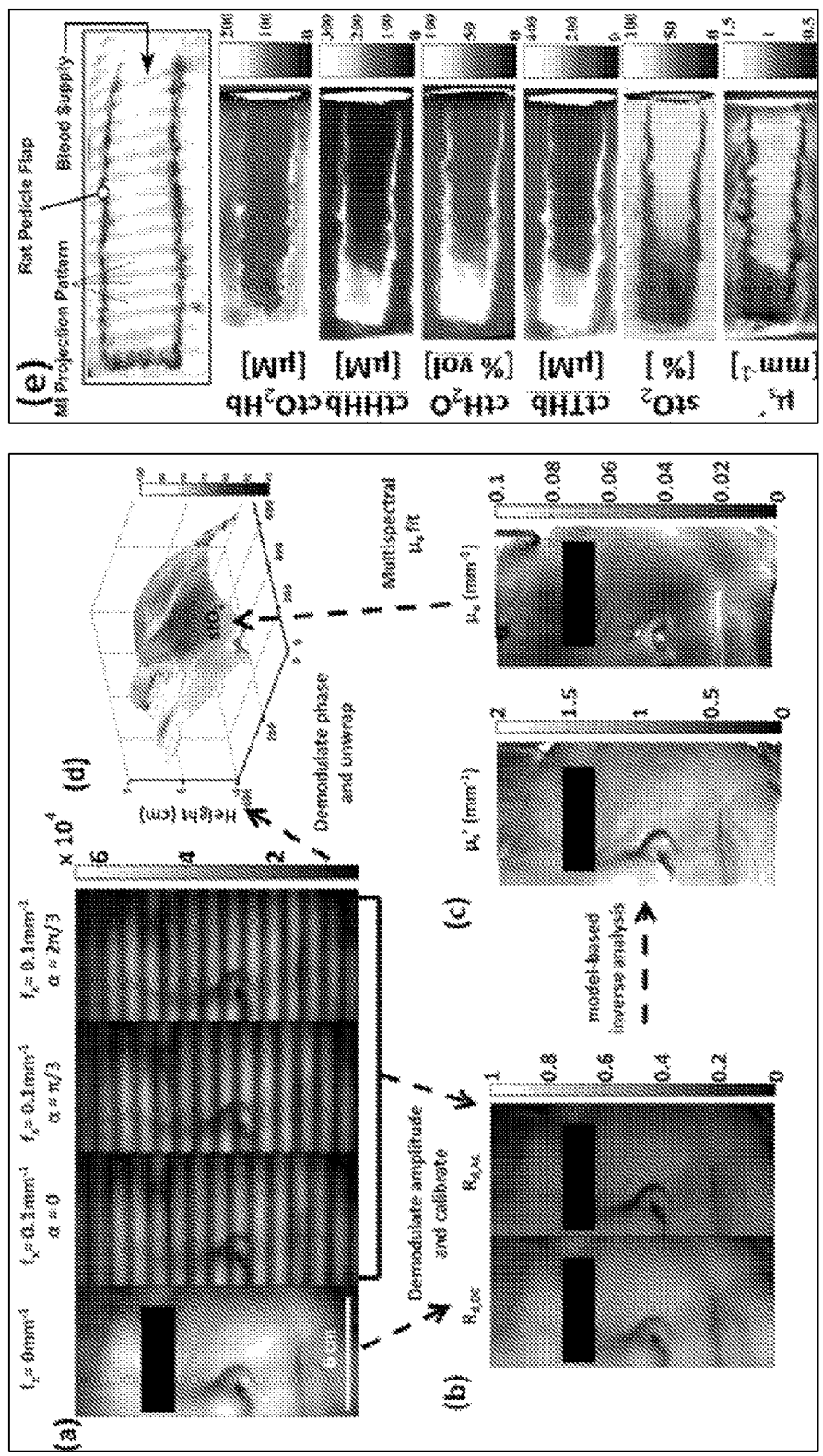
FIG. 1 shows a flowchart of modulated imaging (MI) data processing and typical MI data products. a) shows modulated intensity patterns projected onto the surface. b) shows the patterns amplitude demodulated and calibrated at each frequency (three phase images per frequency). c) shows the patterns fit to a multi-frequency model to determine optical properties. d) shows that phase demodulation separately provides information on tissue height, which can be used for both curvature calibration and visualization. Data are processed for each pixel, generating spatial maps of optical properties. e) shows typical MI data products for a rat pedicle flap, with the distal end demonstrating MI sensitivity to lowered perfusion (stO2), blood pooling (ctHHb & ctTHb), edema (ctH2O), and degradation of matrix ultrastructure/necrosis ($\mu_s'$).
Figure 2:
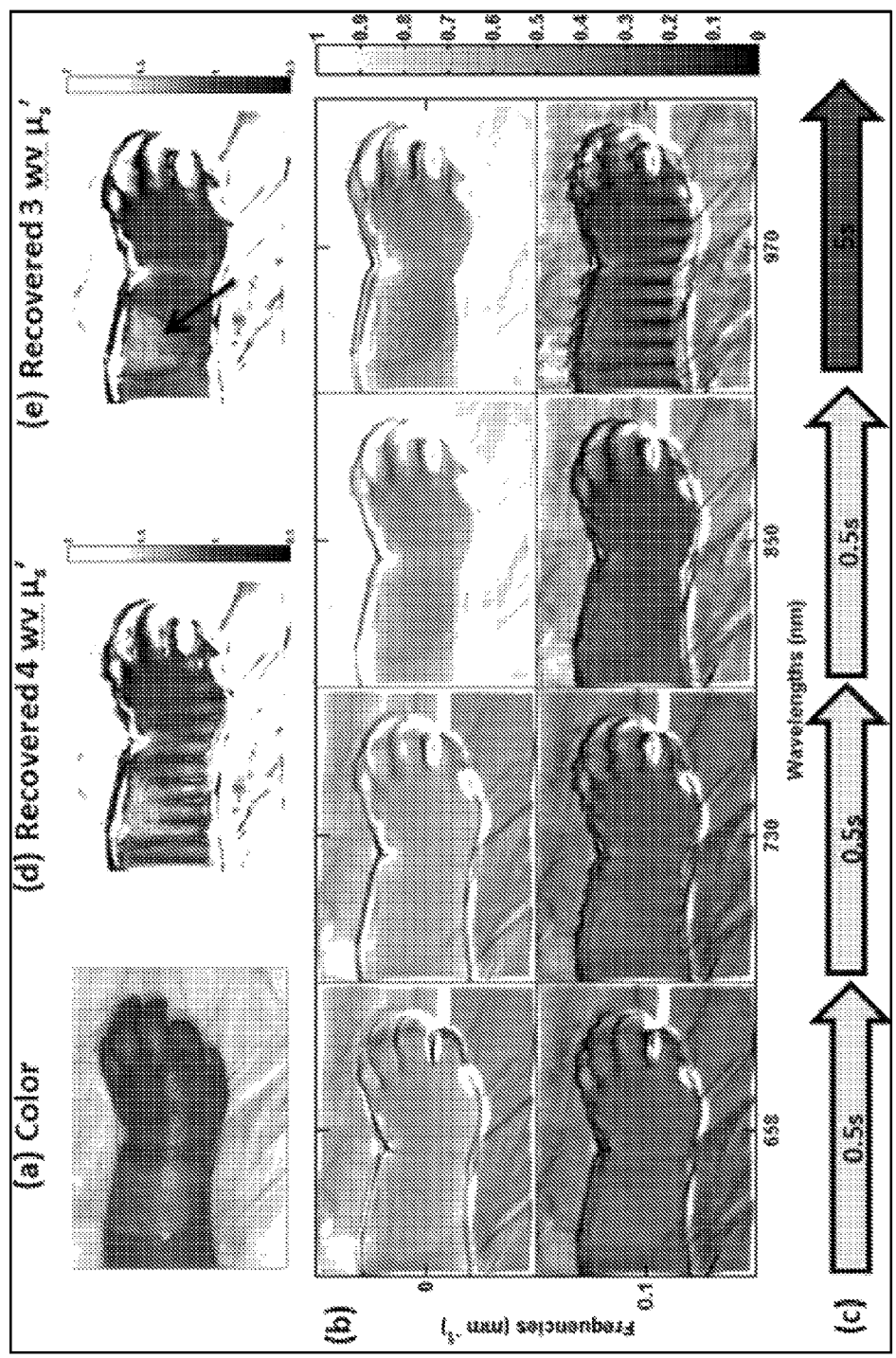
FIG. 2 are images that show that long measurement times in a pediatric burn patient cause visible artifacts in raw and recovered MI data. (a) is a photograph of burn tissue under study; (b) are raw data images showing demodulated diffuse reflectance data at spatial frequency=0.1 mm$^{-1}$ (bottom) and spatial frequency=0 mm$^{-1}$ (top), for 4 wavelengths, from left to right 658 nm, 730 nm, 850 nm, and 970 nm; (c) highlights that a 10× longer integration time (i.e. 5 s) is required to acquire the data set at 970 nm compared to other shorter wavelengths (i.e. only 0.5 s); (d) is an image showing recovered tissue oxygenation (StO2) data, from an analysis including 970 nm data, containing data artifacts; (e) is an image showing recovered tissue oxygenation (StO2) data, from an analysis excluding the demodulated 970 nm data. A black arrow indicates a spatial area of increased oxygenation in the wounded burn region, as compared to the surrounding tissue. This result is obscured in (d) from the motion artifacts associated with the 970 nm measurement.

It should be noted that the figures are not necessarily drawn to scale and that elements of similar structures or functions are generally represented by like reference numerals for illustrative purposes throughout the figures. It also should be noted that the figures are only intended to facilitate the description of the various embodiments described herein. The figures do not necessarily describe every aspect of the teachings disclosed herein and do not limit the scope of the claims.

DESCRIPTION

The embodiments provided herein are directed to systems and methods that facilitate efficient modulated imaging for quantitative characterization of tissue structure and function.

In conventional systems, the same spatially structured light pattern (or patterns) was (were) illuminated at all relevant wavelengths. In one embodiment, an apparatus for increased efficiency modulated imaging system separates the light sources into spatially structured illumination and spatially un-modulated light (planar) illumination. Here planar light is defined as light with substantially no spatial intensity pattern or structure and structured light is defined as light illumination with spatial intensity pattern or structure. The wavelengths of the planar and structured light illuminations are chosen to optimize sensitivity as described below.

Figure 3A:
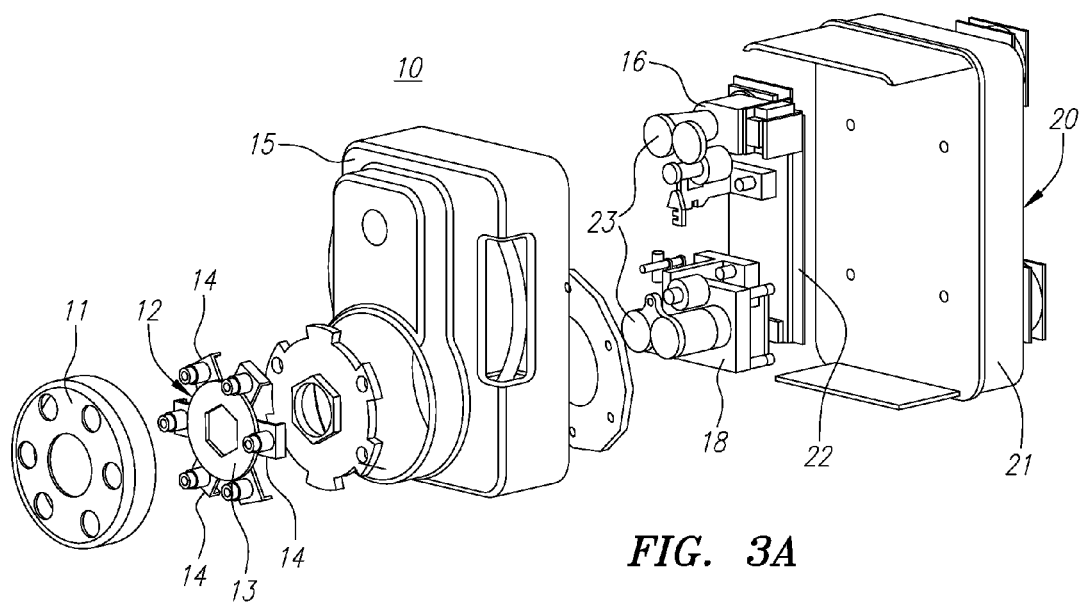
FIG. 3(a) shows an exploded assembly view of an embodiment of an increased efficiency apparatus for modulated imaging showing a light ring for planar external light illumination, a projection system for structured light illumination, and an off-center camera.

FIG. 3(a) shows a preferred embodiment of an increased efficiency modulated imaging apparatus 10. The apparatus 10 comprises an illumination source 12 having a number of external non-structured (planar) light sources 14 on its perimeter and configured to illuminate an area of a tissue sample, a projection system 16 that provides patterned (structured) light to illuminate the area of the tissue sample, and a detector or camera 18 positioned off center from both the projection system 16 and the external planar light source 12 and configured to collect light from the area of the tissue sample illuminated by the projection system 16 and the external planar light source 12. The planar light source 12, projection system 16 and camera 18 are coupled to a printed circuit board (PCB) 22, which includes a processor, power, drivers, memory and software executable on the processor and stored in memory. The light data collected by the camera 18 can be processed using the stored software and processor or ported out to a computer or other processor for processing. The projection system 16, camera 18 and PCB 22 are mounted to an imaging base 20 having a heat sink 21. Two position filters 23 are coupled to the camera 18 and projection system 16.

The external planar light source 12 is shown in FIG. 3(a) as a ring light assembly but could be other externally mounted light sources, including LEDs or lasers, that provide non-spatially structured illumination that does not go through the projection system 16. The ring light assembly includes a plurality of planar light sources 14 positioned about the periphery of a ring base 13. The base 13 along with a cover 11 are externally mounted to a cover 15 of the modulated imaging apparatus 10.

The selection of wavelengths is flexible in both the projection system 16 and planar, non-structured source(s) 12, 14. The projection system 16, which may include a DLP projector, a LOCOS projector, and the like, may comprise a number of switchable light sources such as Light Emitting Diodes (LEDs) of various wavelengths, such as, e.g., the LEDs 17 and 17' shown in FIG. 4 with regard to the planar light source 12, and is capable of providing modulated light of various spatial frequencies or other structured light patterns. The light sources 14 on the external planar illuminator 12 may also be LEDs with one or more wavelengths but specifically provide uniform illumination without spatial structure. The structured projection 16 and external planar light sources 12 are directed to generally the same area on the tissue sample. The camera 18 is off center from both beam axes of the planar light and structured light beam paths and collects light from generally the same area on the tissue sample that has been illuminated. A major benefit of the configuration of the external planar illumination source 12 is increased transfer of non-structured light to the sample due to the relaxed, "non-imaging" constraints which do not require the light to be patterned and optically relayed onto the samples. This configuration improves system efficiency, reduces imaging times to obtain a desired signal-to-noise ratio (SNR), and increases feasibility for applications when measurement times are constrained by practical considerations such as usability and portability.

In a preferred embodiment, the camera 18 is placed behind and off-axis from the external planar source 12, permitting minimal cross-talk from light scattering directly from the source 12 to camera 18. In a preferred embodiment, the camera 18 is a 12-bit monochrome CCD camera but may include any commercial CMOS camera.

Figure 3B:
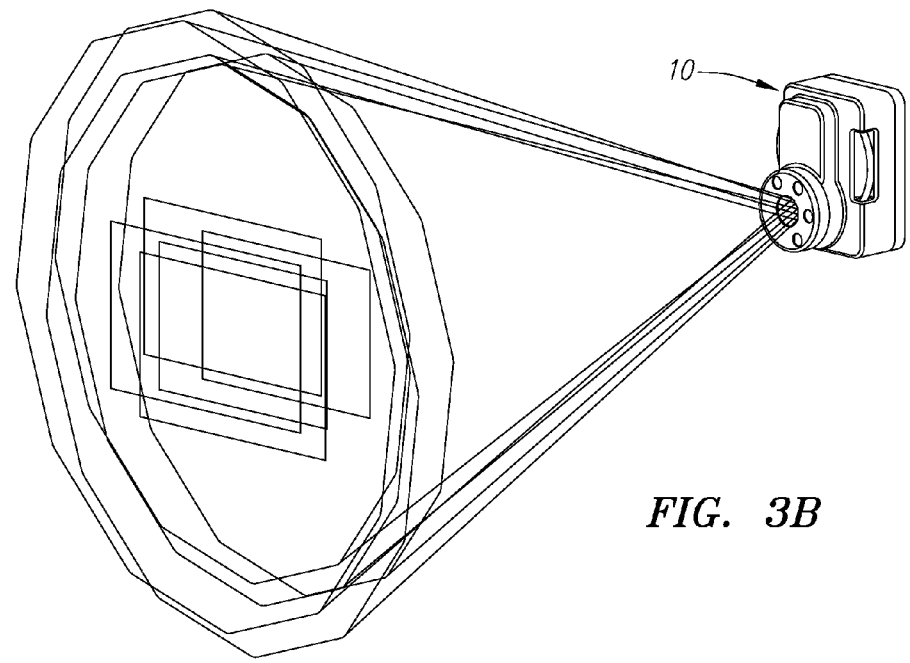
FIG. 3(b) shows an assembled view of the increased efficiency apparatus for modulated imaging and a light ring pattern projected therefrom with a rectangular structured light field in the center, superimposed by planar light illumination both of which are detected by the camera.

In FIG. 3(b) an example shows a configuration where light is imaged through the middle of a collection of sources, oriented in a ring. Other embodiments are possible, but all have the feature that the structured light and planar light sources 16 and 12 are illuminating generally the same area on the tissue sample and that the camera 18 is configured to image generally the same area illuminated by the structured and planar light sources 16 and 12.

Figure 4:
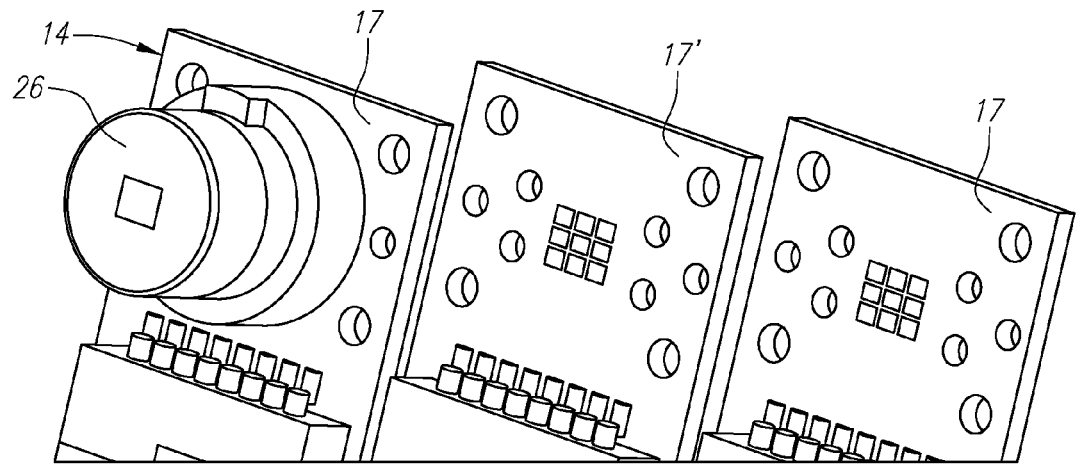
FIG. 4 shows a planar light source with 9 positions to be populated with different wavelength LED.

In another embodiment, as shown in FIG. 4, each light source 14 on the planar source 12 has 9 positions that can be populated with any wavelength, which allows the flexible extension of modulated imaging analysis to biological metrics that are sensitive to other wavelengths, see, e.g., a multiple color LED module 17 and a single color LED module 17', which may be complimentary to the wavelengths used to perform the core modulated imaging (structured light) measurement. Although shown as 9 positions, each light source 14 on the planar light source 12 can have 9 positions, 12 positions, etc.

Figure 5:
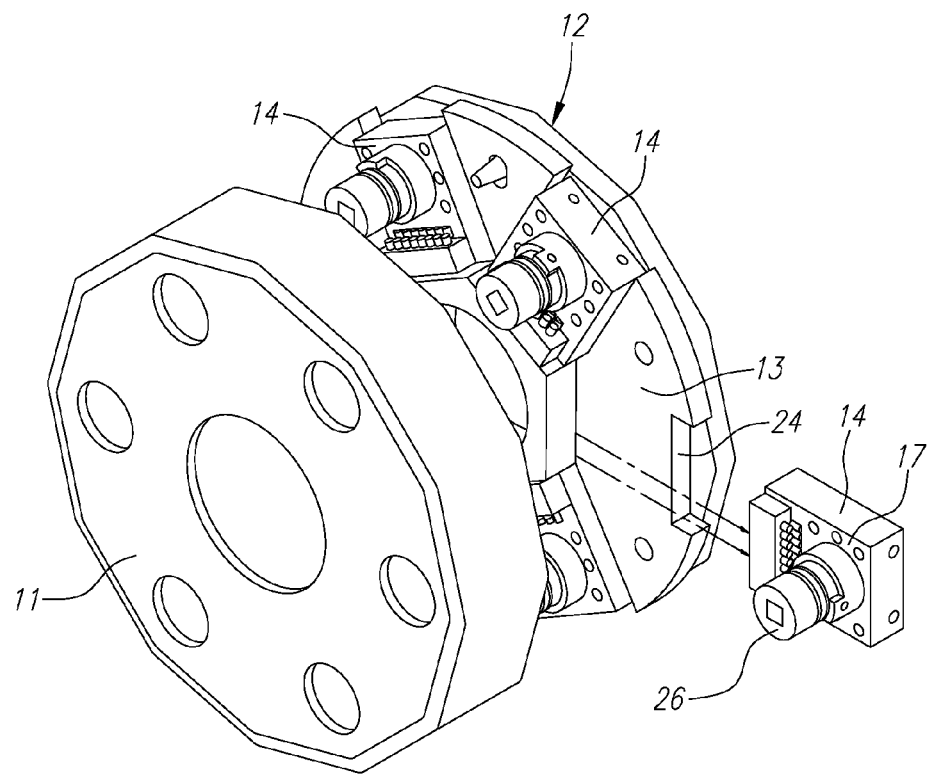
FIG. 5 shows a planar illumination light ring with removable LED modules.

In another embodiment, as shown in FIG. 5, the base 13 of the external planar illuminator 12 provides sockets 24 into which the external light sources 14, such as LED modules 17, can be plugged into or taken out of allowing for a reconfigurable wavelength selection.

In another embodiment, as shown in FIG. 4, each light source 14, e.g. an LED module 17, incorporates a beam homogenizer 26, such as an integrating rod or diffuser, to spatially flatten and combine the output from the multiple individually addressable LED chips on the same source.

Figure 6:
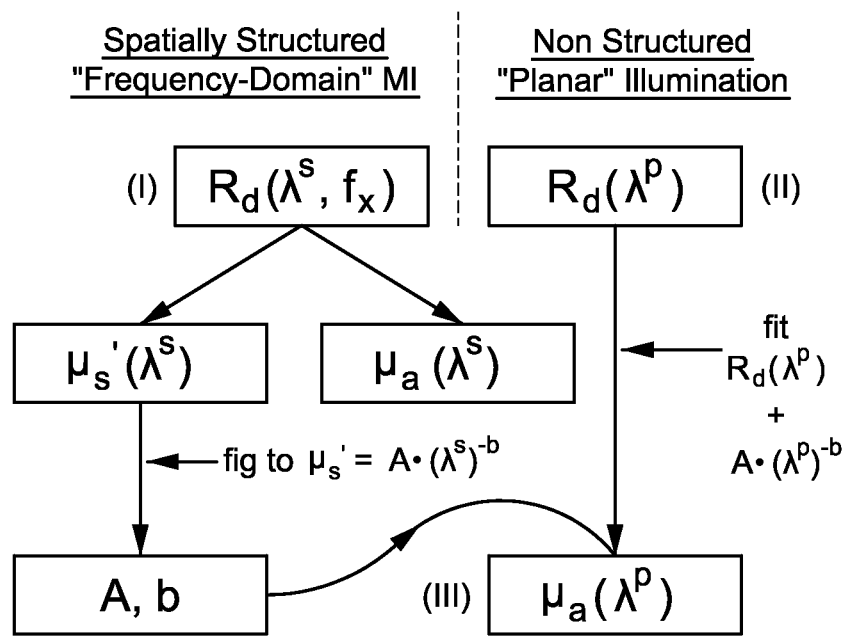
FIG. 6 is a workflow diagram of an efficient MI analysis using structured and non-structured light.
Figure 9A:
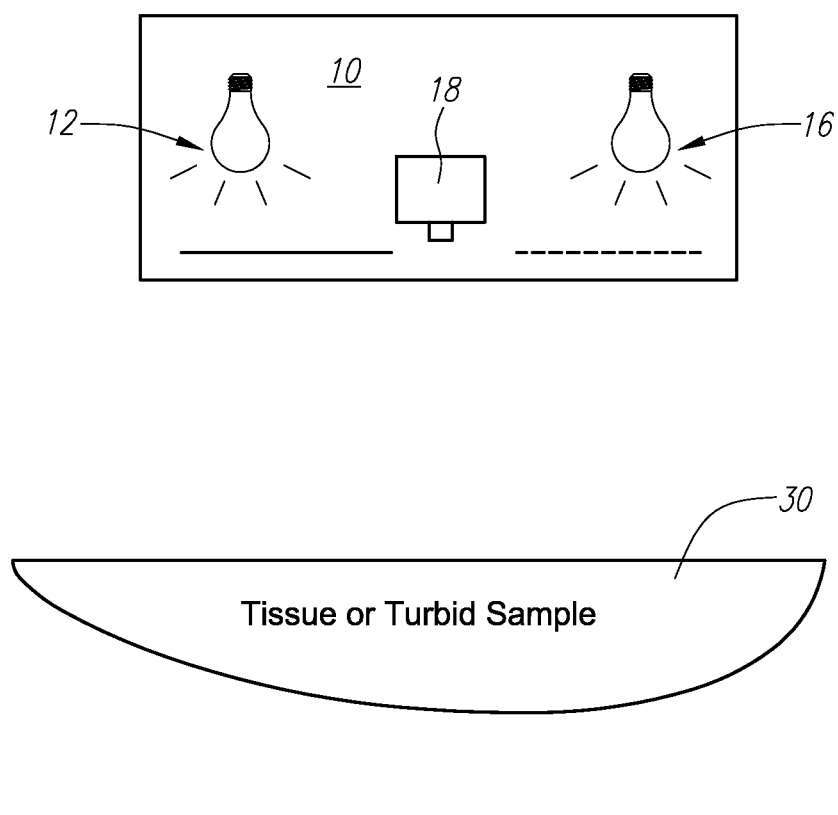
FIG. 9a is a schematic showing an apparatus with light sources configured to illuminate the sample with light not containing spatial structure and light containing spatial structure.
Figure 9B:
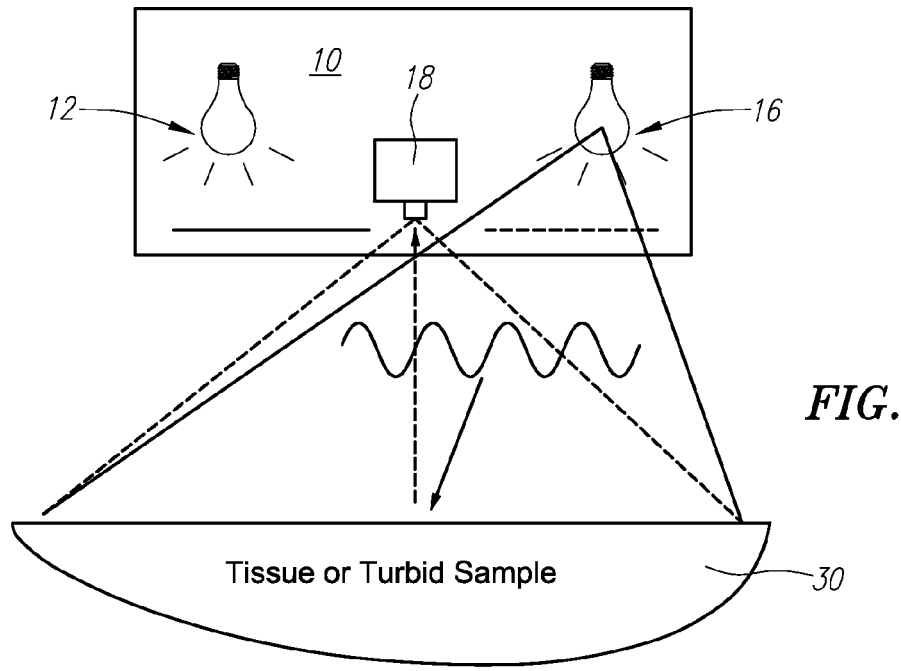
FIG. 9b is a schematic showing the apparatus in FIG. 9a with an illumination condition using the light having spatial structure.
Figure 9C:
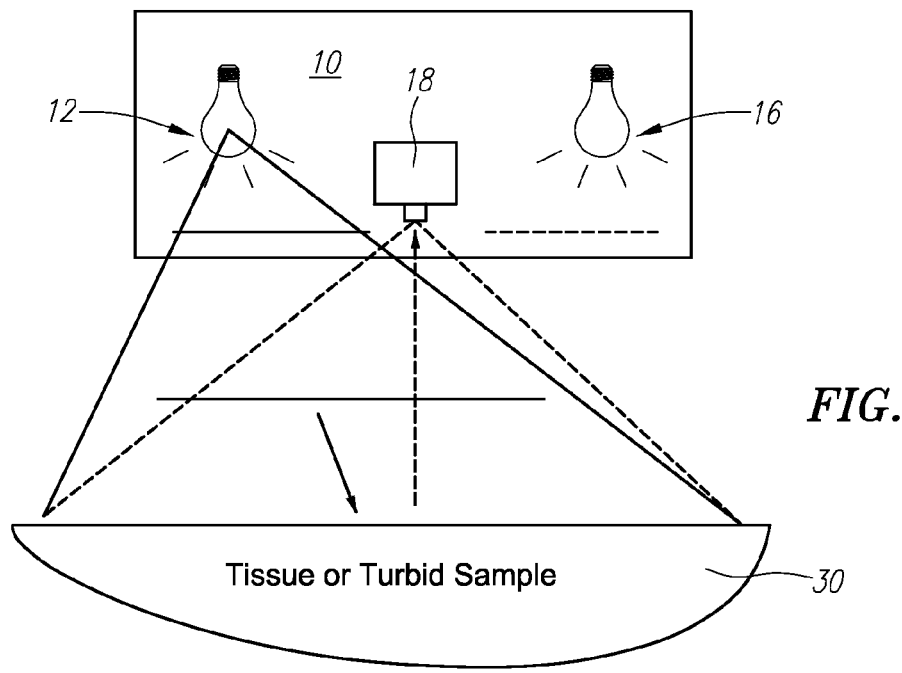
FIG. 9c is a schematic showing the apparatus in FIG. 9a with an illumination condition using the light not having spatial structure.

Method of Operation and Analysis:

The apparatus 10 for modulated imaging is operated as follows. Modulated imaging typically collects data at a number of discrete wavelengths $\lambda_1, \lambda_2, \ldots, \lambda_n$. each of which has a different throughput or signal to noise ratio (SNR) at the camera or detector. The efficient apparatus 10 provided herein separates these n wavelengths into two categories: 1) spatially-structured wavelengths, $\lambda_1^S$, $\lambda_2^S, \ldots, \lambda_j^S$ and non-structured planar wavelengths $\lambda_1^P$, $\lambda_2^P, \ldots, \lambda_k^P$. As described above, the motion artifacts tend to appear for wavelengths for which throughput or signal to noise ratio (SNR) is low. The low SNR may result from a low source power, poor projector-source coupling, reduced projector throughput, low received signal or poor detector sensitivity for that wavelength. A low SNR wavelength requires a correspondingly higher integration, (i.e. camera exposure time), making it susceptible to motion. In a demonstration example of the method provided herein, spatially structured illumination was performed with high SNR wavelengths and non-structured planar illumination was performed with low SNR wavelengths. The efficient apparatus 10 provided herein treats the spatially structured and non-structured light differently in the analysis shown in FIG. 6 and described in the following steps as shown in FIGS. 9b and 9c. As shown schematically in FIG. 9a, the efficient apparatus 10 is shown to include a planar light source 12, a structured light source 16 and a camera 18 positioned above a tissue or turbid sample 30.

1) As shown in FIG. 9b, the structured light sources 16 are turned on and scanned on the tissue sample 30 at one or a small number of high SNR wavelengths (e.g. $\lambda_j^S = \lambda_1^S, \lambda_2^S, \lambda_3^S$), as described briefly in U.S. Pat. No. 6,958,815. The structured light illuminates the sample 30 at these wavelengths with a number of spatial frequencies, and the light reflected and scattered from the sample 30 is collected by the camera 18. This data can then be analyzed to obtain the modulation transfer function and/or optical property information of the sample, for example the spatially-resolved absorption and reduced scattering ($\mu_a(\lambda_j^S)$ and $\mu_s'(\lambda_j^S)$) maps, using either a physical model for scattering of light in biological tissue, or empirical data-lookup based on a catalog of measurements or simulations. Examples of physical models which account for sample turbidity are the Standard Diffusion Equation and Radiative Transport models of light transport.

2) Next, the measurements at spatially structured wavelengths $\lambda_j^S$ can be interpolated or extrapolated to non-structured wavelengths, $\lambda_k^P$, based on the wavelength-dependent features of optical properties in the sample of interest. For example, in the near-infrared region, the derived scattering coefficient $\mu_s'(\lambda_j^S)$ can be fit to a power law function of wavelength such as $\lambda_s'(\lambda) = A^*\lambda^{-b}$, or more generally $\mu_s'(\lambda) = A_1^*\lambda^{-b}_1 + A_2^*\lambda^{-b}_2 + \ldots + A_n^*\lambda^{-b}_n$, interpolated or extrapolated at each pixel in the image detected by the camera 18 to provide an estimated value for the scattering coefficient for the non-structured wavelengths, $\mu_s'$ ($\lambda_k^P$). For the stated equations A and b parameters are free, non-negative variables, and n is at least 1. Note that by deriving property such as the scattering coefficient for a non-structured (ie. low SNR) wavelength from the structured (high SNR) wavelength data, imaging time can be reduced by eliminating the need to acquire structured light images to directly measure $\mu_s'$ ($\lambda_k^P$). This permits use of a single non-structured light pattern to determine the remaining parameter, $\mu_a$, ($\lambda_k^P$) hence reducing overall acquisition time and avoiding motion artifacts.

3) As shown in FIG. 9c, the structured light sources 16, which are at high SNR wavelengths, are then turned off, and the planar light sources 12, which are low SNR wavelengths, are then turned on and used to illuminate the sample 30. The light reflected from the sample 30 is detected by the camera system 18, providing remitted light at the desired wavelengths, such as the diffuse reflectance coefficients, Rd $\lambda_k^P$. As an illustrative example, the diffuse reflectance is measured at 970 nm to determine $ctH_2O$ sensitivity. Note that this Step can alternatively be performed before Step 1, or interleaved with measurements within Step 1.

4) In the last step of the analysis the optical properties at the low SNR wavelengths, $\lambda_k^P$ are calculated by using the combination of planar and extrapolated or interpolated structured light source measurements. For example, diffuse reflectivity values ($R_d(\lambda_k^P)$) and the fitted scattering coefficients ($\mu_s'(\lambda) = A^*\lambda^{-b}$ evaluated at $\lambda_k^P$; i.e. $\mu_s'(\lambda_k^P) = A^*(\lambda_k^P)^{-b}$) can be combined with a 1-parameter fit or lookup-table calculation using a physical scattering/reflection model for biological tissue, hence yielding $\mu_a(\lambda_k^P)$.

5) At this stage the optical property (e.g. scattering and absorption) coefficients are fully determined for all wavelengths measured directly from the modulation transfer function for data derived from structured illumination wavelengths (ie. high SNR) and light data derived from non-structured planar illumination wavelengths (ie. low SNR).

6) Chromophore concentrations and physiology indices can now be derived from the full wavelength dependent scattering and absorption coefficients.

Note that Steps 2, 4 and/or 6 can be performed at any stage post-measurement of the underlying data. Moreover, instead of being performed sequentially, Steps 2, 4 and/or 6 can be performed together in a direct "global" fit, or simultaneous analysis of all the input data to provide the desired output, such as to obtain the concentration of absorbing or fluorescent molecules.

Figure 7:
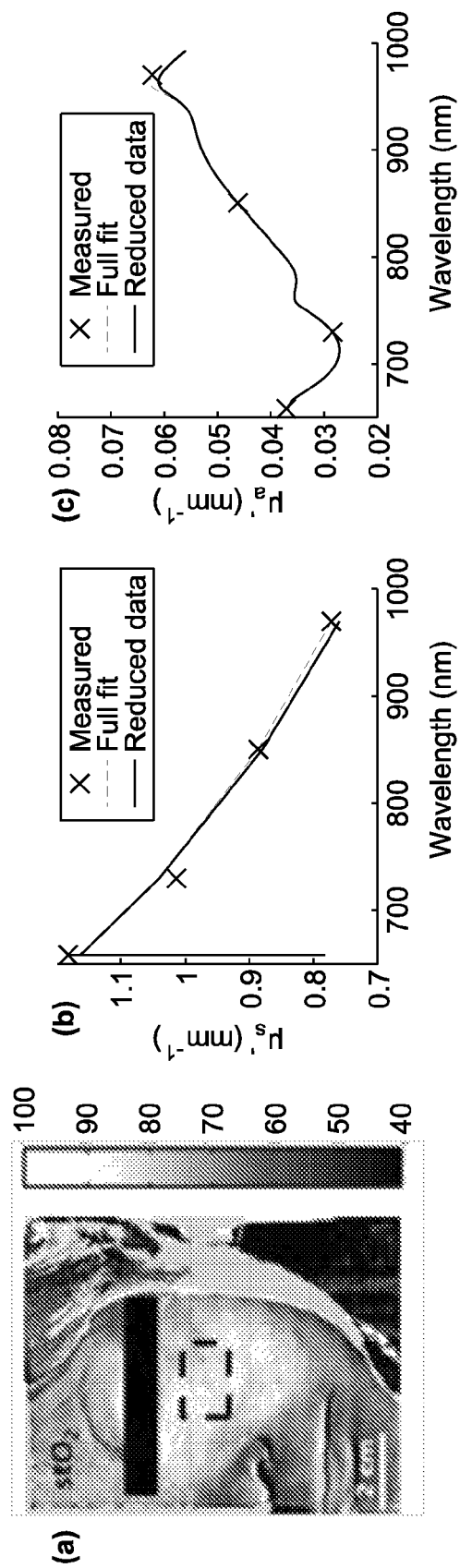
FIG. 7 shows example data showing a comparison between scattering and absorption coefficients obtained from the modulated imaging apparatus described in prior art and the present efficient modulated imaging apparatus and method. (a) is an image of a 'Port Wine Stain (PWS)' imaged with a prior art apparatus. Note that the PWS region on the cheek has a higher stO2 concentration compared to the surrounding areas due to increased vascularization. (b) is a graph of the scattering coefficient as a function of wavelength comparing prior art (full fit line) and efficient apparatus and method of the present invention (reduced data lines). (c) is a graph of the absorption coefficient as a function of wavelength comparing prior art (full fit line) and efficient apparatus and method of the present invention (reduced data lines)

FIG. 7 shows an example comparison between 1) a full modulated imaging analysis as obtained by the system prescribed by prior art (full fit lines), and 2) the present efficient apparatus and method with reduced number of wavelengths (reduced data lines). There is excellent agreement between the two apparatus and methods. Note, however, that the advantage of the present efficient apparatus is in removal of motion artifacts while providing good fidelity in the optical property (e.g. scattering and absorption) coefficients at all wavelengths.

Figure 8:
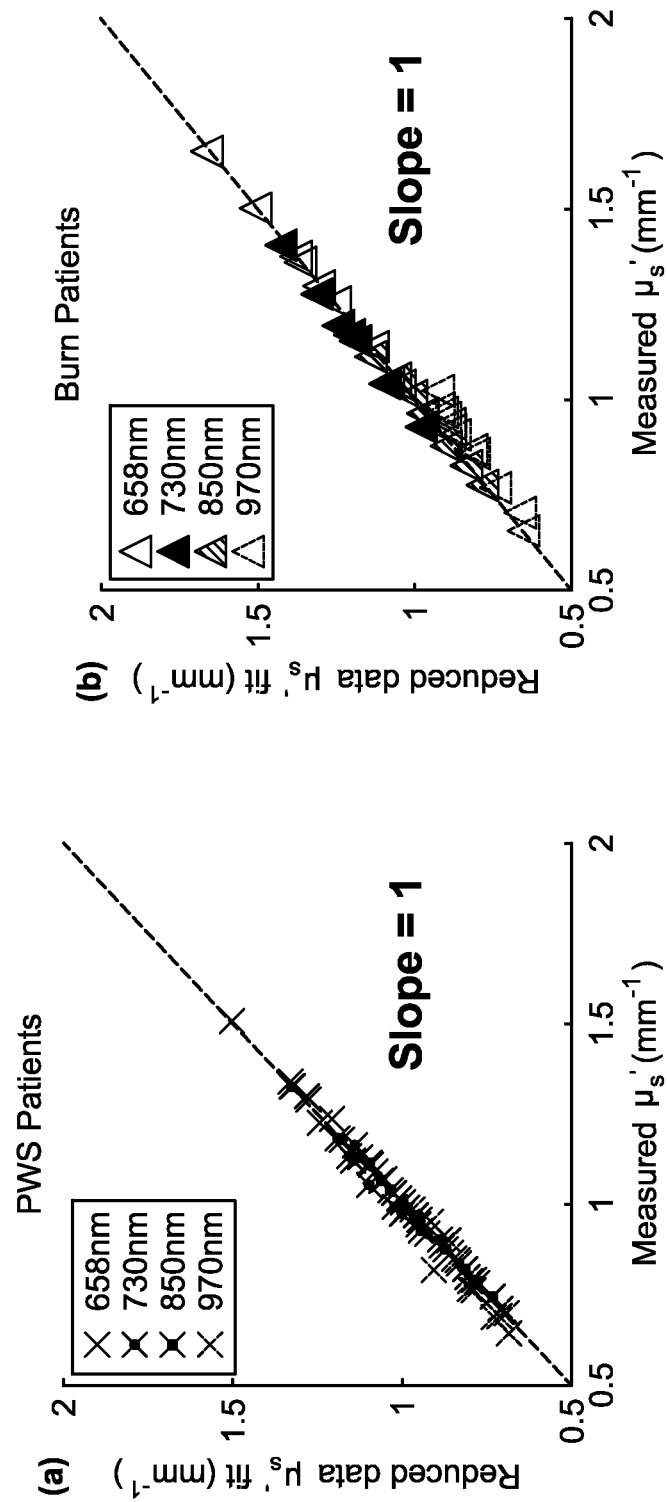
FIG. 8 are graphs showing a comparison of extracted scattering and absorption data from a Port Wine Stain (a) and Burn tissue (b) using the efficient modulated imaging apparatus (y axis) versus using prior art modulated imaging apparatus (x axis).

To assess the scope of measurements and patient populations that could be addressed with this refined method, 10 port-wine stain and 10 burn patient measurements were collected and analyzed with a prior art apparatus and method as well as the efficient modulated imaging apparatus 10 and method presented here. FIG. 8 shows plots of scattering (FIG. 8a) and absorption coefficients (FIG. 8b) for various wavelengths obtained by the present efficient apparatus (y axis) versus that obtained from the prior art apparatus (x axis). These data are diverse in terms of their absorption coefficients: blood pooling in PWS cases and tissue blanching/loss of epidermal melanin in burn cases exhibit high- and low-absorption, respectively. Nevertheless, FIG. 8 shows a one-to-one correspondence of the two as indicated by a straight line with slope=1.

In the present description the term camera refers to an optical detection system which images an area of a tissue sample onto an array of pixilated detectors, where the area of the sample imaged is much larger than the smallest spatial feature of the structured light illumination. In another embodiment the light reflected from the sample is collected by a single detector, such that light is collected from an area of the sample which is smaller than the smallest spatial feature of the structured light illuminating it from the projection system.

Recently, an MI system embodiment implemented both LED flood (unstructured) illumination on the front of the instrument, as well as standard MI LED-based structured projection from a Digital Micromirror Device.

Figure 10:
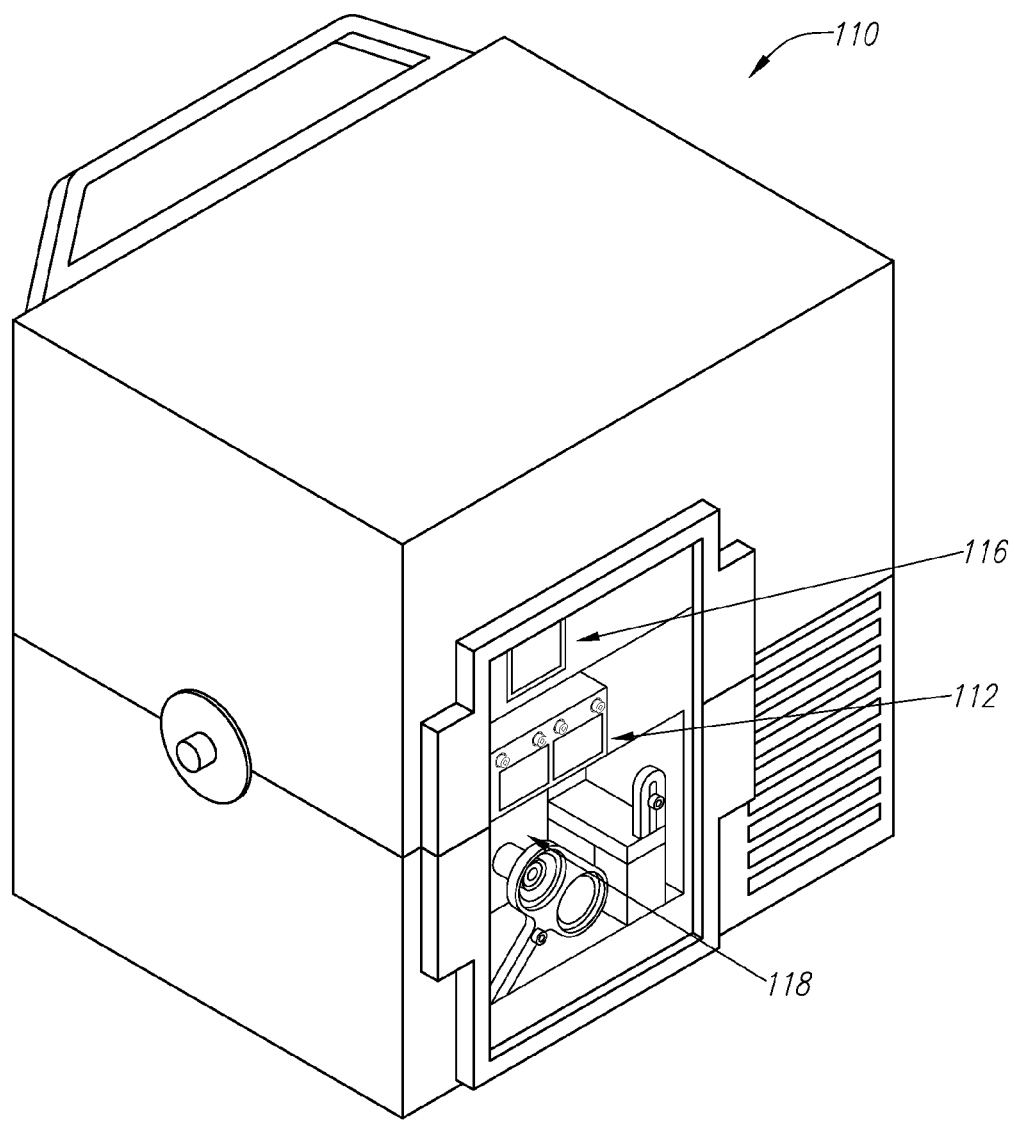
FIG. 10 shows an embodiment of a modulating imaging instrument with structured and unstructured light sources, and an off axis camera.

FIG. 10 shows an embodiment of an MI device 110 with structured 116 and unstructured light 112 sources. A camera 118 is configured to view both structured and unstructured light reflecting off of a target positioned approximately one foot (1') in front of the instrument.

Figure 11:
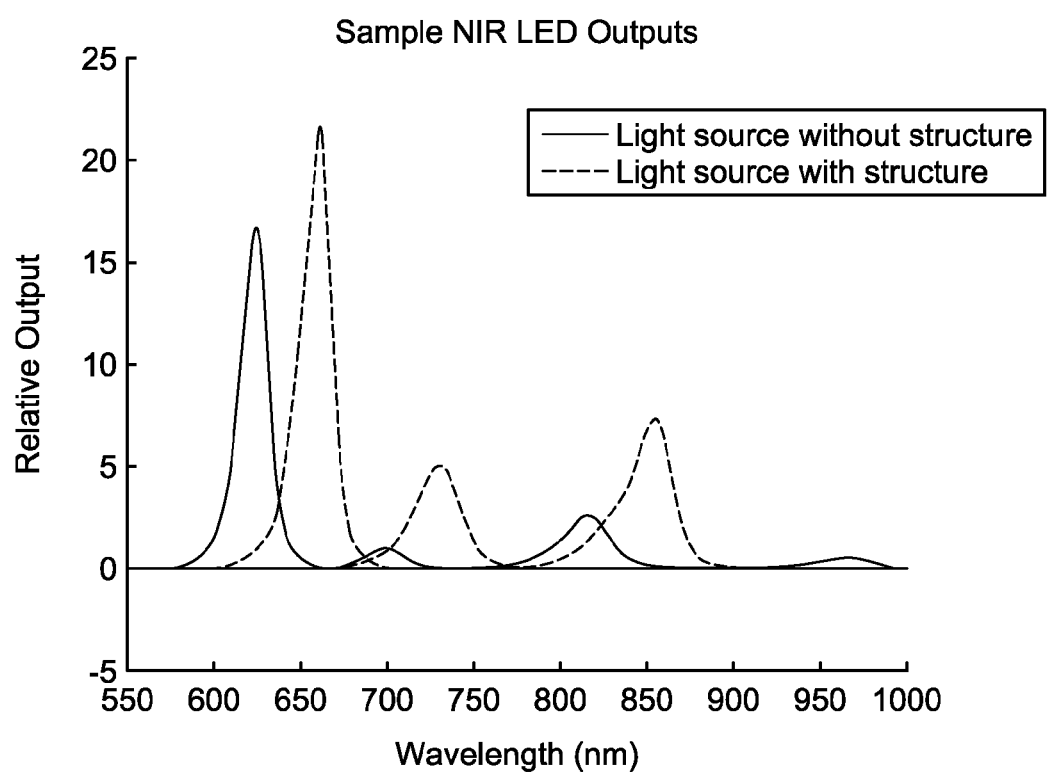
FIG. 11 is a graph showing an example of the relative efficiency of typical LEDs.

FIG. 11 shows an example of the relative efficiency of typical LEDs. Weak wavelengths (low peak values) result in poor imaging speed when required to emit through the projector. These are optimal candidates for flood (unstructured) illumination, avoiding the need to use a low-light-throughput (low etendue) projector.

Figure 12:
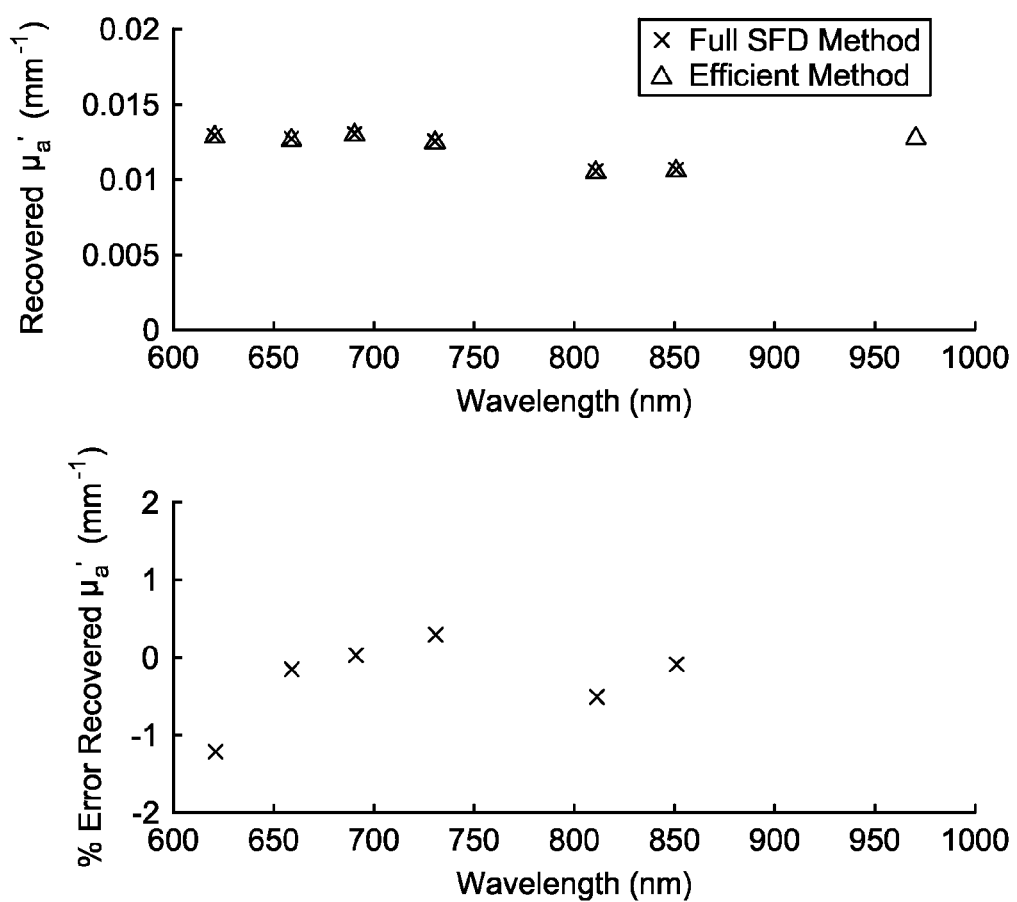
FIG. 12 are graphs showing (top) a comparison of Full and Efficient methods for recovery of absorption optical properties, and (bottom) a comparison, in percent deviation from the "gold standard" full analysis, shows generally less than 1% difference in accuracy between the approaches, thus validating the Efficient method.

FIG. 12 (top) shows a comparison of Full and Efficient methods for recovery of absorption optical properties. A measurement of a standardized tissue-simulating phantom with known optical properties was used as an imaging target. For the Full analysis, standard spatial frequency domain measurements were performed. For the Efficient analysis, a subset of the Full analysis was performed for 3 wavelengths (620, 690, 810 nm), and then optical scattering values were extrapolated or interpolated to the other desired wavelengths (660, 730, 850, 970 nm) to obtain the absorption coefficient with unstructured (planar) data only. This was repeated "in reverse" with structured (660, 730, 850 nm) and unstructured (620, 690, 810 nm) wavelengths. Bottom: A comparison, in percent deviation from the "gold standard" full analysis, shows generally less than 1% difference in accuracy between the approaches, thus validating the Efficient method.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

In the description above, for purposes of explanation only, specific nomenclature is set forth to provide a thorough understanding of the present disclosure. However, it will be apparent to one skilled in the art that these specific details are not required to practice the teachings of the present disclosure.

The various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter.

It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art. For example, the reader is to understand that the specific ordering and combination of process actions described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed:

1. A method for measurement of a turbid sample, the method comprising the steps of:
    illuminating with a first light source a target area of the turbid sample with only spatially structured at a plurality of wavelengths and along a first optical projection path,
    collecting light reflected from the turbid sample to obtain remitted spatially structured light of the sample at a first plurality of wavelengths, $\lambda_j$,
    illuminating with a second light source the target area of the turbid sample with only planar structured light at a plurality of wavelengths and along a second optical projection path, wherein the first optical projection path differs from the second optical projection path,
    collecting light reflected from the turbid sample to obtain remitted planar structured light of the sample at a second plurality of wavelengths, $\lambda_k$, and
    combining measurements of the remitted spatially structured light and the remitted planar light collected from the turbid sample to obtain fit parameters, wherein the fit parameters include one or more optical properties of the turbid sample at the first and second plurality of wavelengths, $\lambda_j$ and $\lambda_k$, and a concentration of absorbing or fluorescent molecules.

2. The method of claim 1, wherein each wavelength of the first plurality of wavelengths, $\lambda_j$, has a different signal to noise ratio (SNR) and wherein each wavelength of the second plurality of wavelengths, $\lambda_k$, has a different signal to noise ratio (SNR).

3. The method of claim 2, wherein the first plurality of wavelengths, $\lambda_j$, differs from the second plurality of wavelengths, $\lambda_k$.

4. The method of claim 3, further comprising, prior to illuminating the target area of the turbid sample with only non-spatially structured light, extrapolating the measurements of the remitted light having spatial structure to calculate a scattering coefficient for the second plurality of wavelengths, $\mu'(\lambda_k^P)$.

5. The method of claim 4, wherein the measurements of the remitted non-spatially structured light are at diffuse reflectance coefficients, $Rd\lambda k^P$.

6. The method of claim 5, wherein $\mu'(\lambda_k^P)$ and $Rd\lambda k^P$ are combined to yield $\mu_a(\lambda_k^P)$.

7. The method of claim 6, wherein the signal to noise ratios (SNR) of the first plurality of wavelengths, $\lambda_j$, are higher in relation to the signal to noise ratios (SNR) of the second plurality of wavelengths, $\lambda_k$.

* * * * *